US00PP28101P2

(12) United States Plant Patent
van der Hoorn

(10) Patent No.: US PP28,101 P2
(45) Date of Patent: Jun. 13, 2017

(54) *COTYLEDON* PLANT NAMED 'HOCO01'

(50) Latin Name: *Cotyledon undulata*
Varietal Denomination: HOCO01

(71) Applicant: Cornelis Antonius Joseph van der Hoorn, Nieuwveen (NL)

(72) Inventor: Cornelis Antonius Joseph van der Hoorn, Nieuwveen (NL)

( * ) Notice: Subject to any disclaimer, the term of this patent is extended or adjusted under 35 U.S.C. 154(b) by 0 days.

(21) Appl. No.: 14/999,196

(22) Filed: Apr. 8, 2016

(51) Int. Cl.
*A01H 5/12* (2006.01)

(52) U.S. Cl.
USPC ..... Plt./263.1

(58) Field of Classification Search
USPC ..... Plt./263.1
See application file for complete search history.

*Primary Examiner* — Annette Para
(74) *Attorney, Agent, or Firm* — Samuel R. McCoy, Jr.

(57) ABSTRACT

A new and distinct *Cotyledon undulata* cultivar named 'HOCO01' which is characterized by a globular plant shape, moderate to strong branching, near-orbicular leaves with heavily undulated margins, a unique cupped to undeeply tubular leaf aspect, a hastate to tubular leaf base, and the stability of these characteristics from generation to generation.

3 Drawing Sheets

Latin name of the genus and species: The Latin name of the genus and species of the novel variety disclosed herein is *Cotyledon undulata.*

Variety denomination: The inventive variety of *Cotyledon undulata* disclosed herein has been given the variety denomination 'HOCO01'.

BACKGROUND OF THE INVENTION

Parentage: 'HOCO01' is the result of a spontaneous whole-plant mutation of the species *Cotyledon undulata* which was discovered at the inventor's commercial greenhouse in Nieuwveen, the Netherlands. In April of 2011, the inventor discovered a mutation of *Cotyledon undulata* which exhibited small, tubular foliage and a heavily undulated leaf margin. The mutation was isolated and grown to a mature size in order to confirm the distinctness and stability of the characteristics first observed. Upon confirmation of distinctness and stability, 'HOCO01' was selected for commercialization in April of 2013.

Asexual Reproduction: Asexual reproduction of the new cultivar 'HOCO01', by way of stem cuttings, was first initiated in April of 2013 at the inventor's commercial greenhouse in Nieuwveen, the Netherlands. Through two subsequent generations, the unique features of this cultivar have proven to be stable and true to type.

SUMMARY OF THE INVENTION

The cultivar 'HOCO01' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'HOCO01'. These characteristics in combination distinguish 'HOCO01' as a new and distinct *Cotyledon undulate* cultivar:

1. 'HOCO01' exhibits moderate to strong branching and a globular plant shape; and
2. 'HOCO01' exhibits small, near-orbicular foliage with a heavily undulated leaf margin; and
3. 'HOCO01' exhibits foliage which is moderately cupped to undeeply tubular, with a hastate to tubular leaf base.

BOTANICAL DESCRIPTION OF THE PLANT

Figure 1:
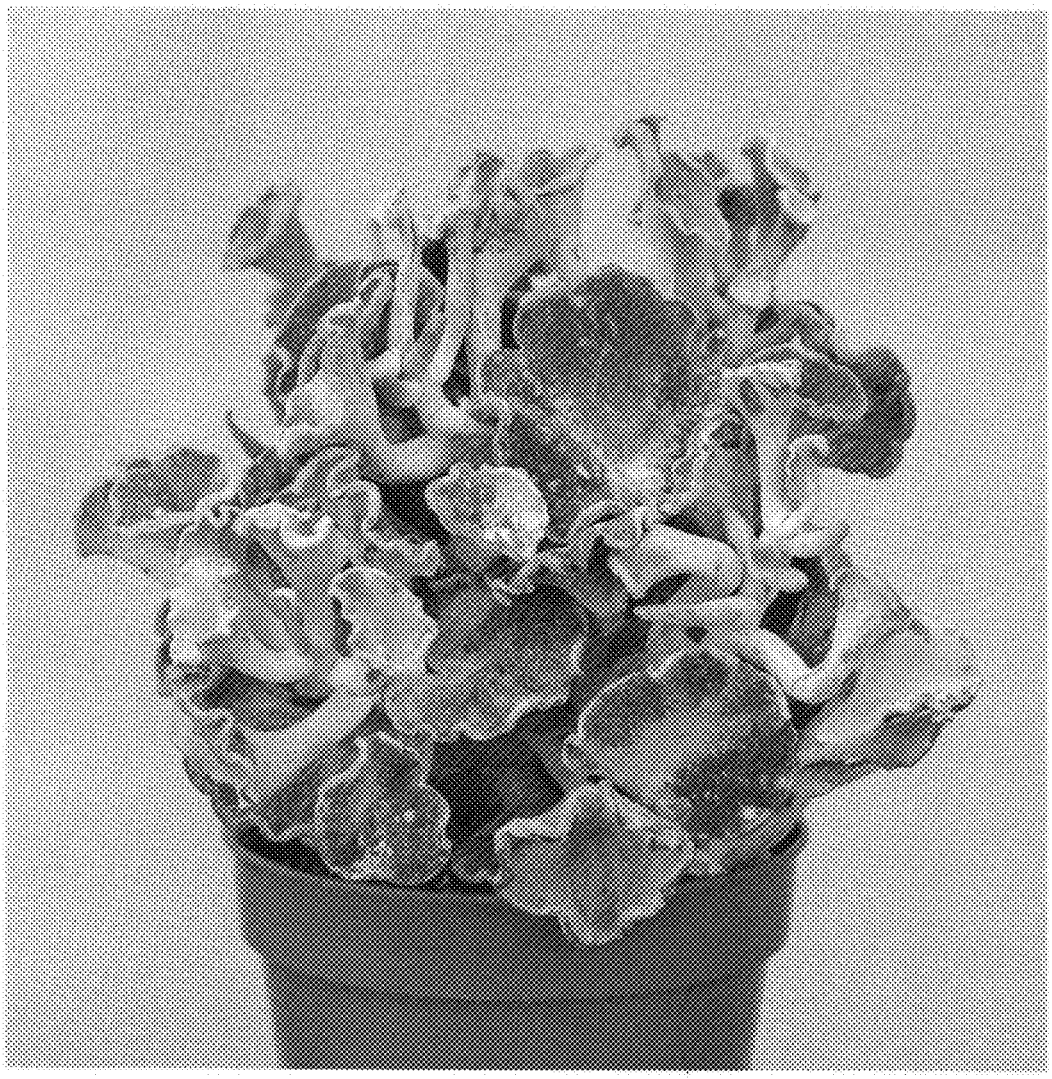
FIG. 1 illustrates, as nearly true as it is reasonably possible to make the same in color photographs of this type, an exemplary plant of 'HOCO01' grown in a commercial greenhouse in Nieuwveen, the Netherlands. This plant is approximately 1.5 years old, shown planted in a 15 cm container.
Figure 2:
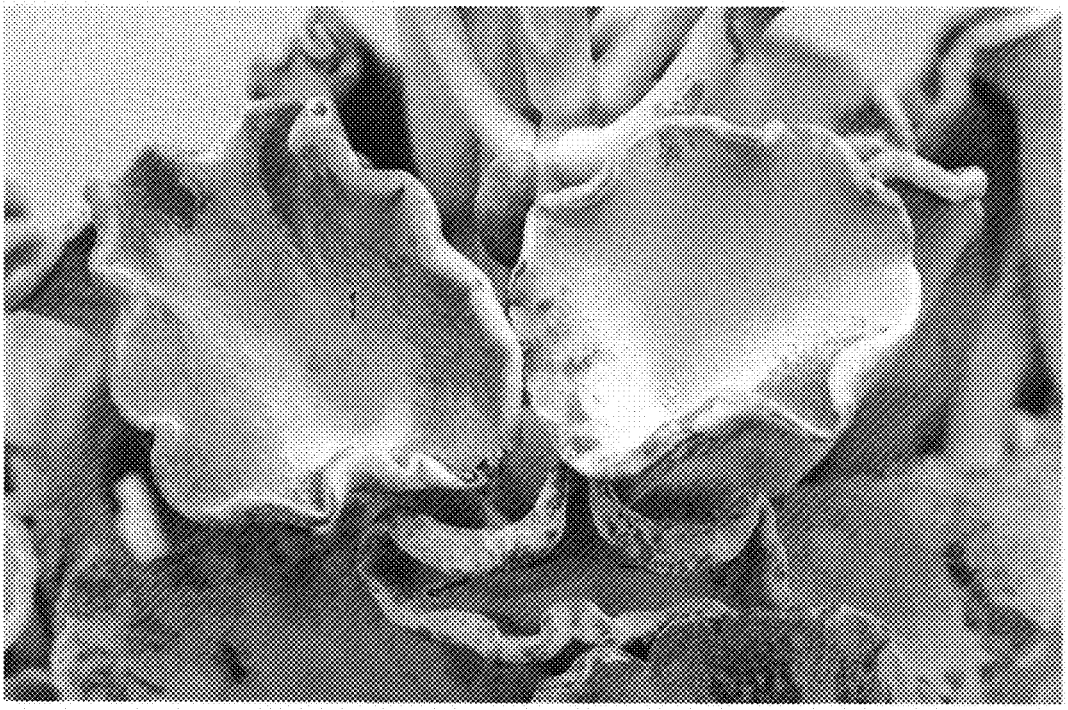
FIG. 2 illustrates, as nearly true as it is reasonably possible to make the same in color photographs of this type, the typical mature foliage habit of 'HOCO01'.
Figure 3:
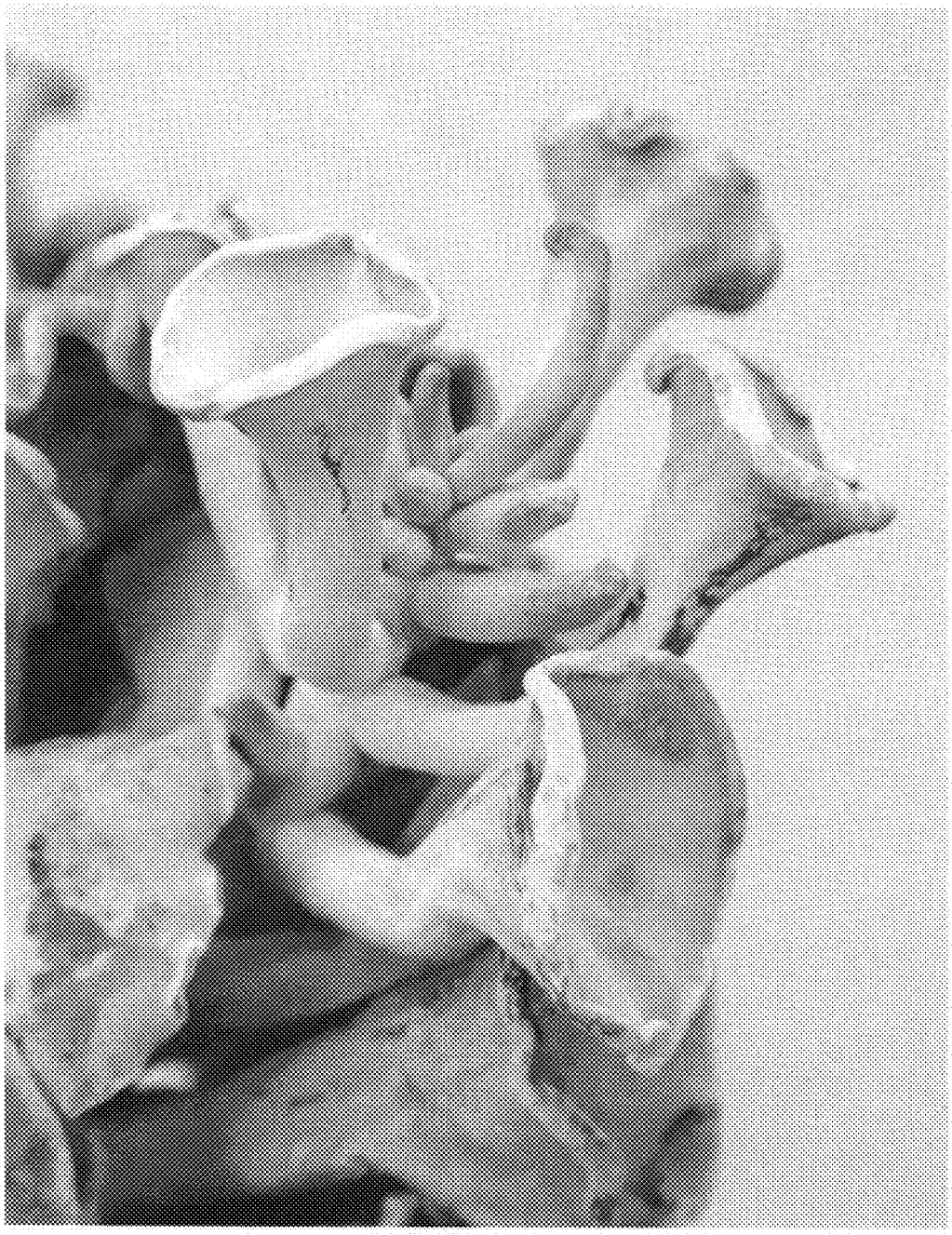
FIG. 3 illustrates, as nearly true as it is reasonably possible to make the same in color photographs of this type, the typical juvenile foliage habit of 'HOCO01'.

The following observations and measurements made in February of 2016 describe averages from a sample set of six specimens of 1.5 year-old 'HOCO01' plants grown in 15 cm nursery containers at commercial greenhouse in Nieuwveen, the Netherlands. Plants were produced using conventional greenhouse production protocols which consisted of flood benches for irrigation, scheduled liquid fertilizer applications, and chemical pest and disease control measures as required. Plants were grown under approximately 50% shade and no photoperiodic treatments or artificial light was given to the plants.

Those skilled in the art will appreciate that certain characteristics will vary with older or, conversely, with younger plants. 'HOCO01' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climatic and cultural conditions. Color notations are based on *The Royal Horticultural Society Colour Chart*, The Royal Horticultural Society, London, 2015 (sixth edition).

A botanical description of 'HOCO01' and a comparison with the parent and closest known comparator, *Cotyledon undulata*, is provided below.

Plant description:

*Growth habit*.—Succulent perennial with a broad, upright growth habit.

*Plant shape*.—Globular.

*Height from soil level to top of foliar plane*.—19.8 cm, on average.

*Plant spread*.—Average of 22.4 cm.

*Growth rate*.—Slow to moderately fast.

*Plant vigor*.—Low to moderate.

*Propagation*.—Type — Stem cuttings. Time to produce a rooted cutting — Approximately 14 days at 16 degrees Celsius. Crop time — Approximately 1 year to produce a marketable plant in a 9 cm container. Pinching is not required to produce a well-shaped plant, but it does promote branching.

*Disease and pest resistance or susceptibility*.—Similar to the parent, *Cotyledon undulata*.

*Environmental tolerances*.—Adapt to, at least, USDA Zones 10 to 13 and temperatures as high as 40 degrees Celsius; low to moderate tolerance to rain; moderate to high tolerance to wind.

Root system:

*General*.—Fine, well-branched fibrous roots.

Stems:

*Branching habit*.—Basal branching, with one primary stem and nine lateral branches, on average.

*Dimensions*.—Primary stem varies with age; lateral branches are 8.7 cm long and 0.9 cm in diameter, on average.

*Internode length*.—1.5 cm, on average.

*Appearance and shape*.—Succulent, moderately thick and rounded.

*Luster*.—Matte; covered with a matte waxy layer.

*Pubescence*.—Glabrous.

*Aspect*.—Average angle of 50 degrees from vertical.

*Strength*.—Moderately strong to strong.

*Color, juvenile*.—Yellow-green, RHS 145C, and covered with a waxy layer, colored greyed-green RHS 192C.

*Color, mature*.—Yellow-green, RHS 145A to 145B, covered with a waxy layer, colored greyed-green, RHS 192C.

*Color at internodes*.—Yellow-green, RHS 145A to 145B, covered with a waxy layer, colored greyed-green, RHS 192C.

Foliage:

*Arrangement*.—Opposite.

*Attachment*.—Petiolate.

*Quantity*.—Approximately 12 leaves per lateral branch.

*Shape*.—Thick, succulent leaves which are near orbicular.

*Dimensions*.—5.7 cm long by 5.3 cm wide and 0.6 cm thick, on average.

*Aspect*.—Moderately cupped to undeeply tubular.

*Apex*.—Rounded.

*Base*.—Hastate to tubular.

*Margin*.—Strongly undulate.

*Pubescence, texture and luster of adaxial surface*.—Glabrous, smooth, and matte; covered with a thin waxy layer.

*Pubescence, texture and luster of abaxial surface*.—Glabrous, smooth, and matte; covered with a thin waxy layer.

*Color*.—Juvenile foliage, adaxial surface — Green, RHS 137B to 137C, and covered with a thin waxy layer, colored greyed-green RHS 188C. Juvenile foliage, abaxial surface — Green, RHS 137D, and covered with a thin waxy layer, colored greyed-green RHS 190D. Mature foliage, adaxial surface — Green, RHS NN137A to NN137B, and covered with a thin waxy layer, colored greyed-green RHS 188C. Mature foliage, abaxial surface — Green, in between RHS 137C and 143A, and covered with a thin waxy layer, colored greyed-green RHS 190D.

*Venation*.—No venation is visible.

*Petiole*.—Dimensions — 3.2 cm long by 0.9 cm wide, on average. Texture, pubescence, and luster — Smooth, glabrous and matte. Strength — Medium. Color, upper and lower surfaces — Yellow-green, in between RHS 145A and 147C, and covered with a thin waxy layer colored greyed-green, RHS 189D.

Inflorescence: No flowering has been observed to date.

COMPARISONS WITH THE PARENT PLANT AND CLOSEST KNOWN COMPARATOR

Plants of the new cultivar 'HOCO01' differ from the parent, *Cotyledon undulata*, which is also the closest known comparator, in the following characteristics:

1. 'HOCO01' exhibits a near globular plant shape, whereas the parent exhibits a broad oblong plant shape.
2. 'HOCO01' exhibits moderate to strong branching, whereas the parent is sparsely branched.
3. 'HOCO01' exhibits near orbicular foliage, whereas the foliage of the parent exhibits a broad flabellate shape.
4. The leaf aspect of 'HOCO01' is moderately cupped to undeeply tubular, whereas the leaf aspect of the parent is flat.
5. On average, the leaves of 'HOCO01' are 5.7 cm long and 5.3 cm wide, whereas the leaves of the parent are 6.6 cm long and 6.7 cm wide.
6. The leaf margins of 'HOCO01' are heavily undulated, whereas the leaf margins of the parent are lightly to moderately undulated.
7. The leaf base of 'HOCO01' is hastate to tubular, whereas the leaf base of the parent is cuneate.

That which is claimed is:

1. A new and distinct variety of *Cotyledon undulata* plant named 'HOCO01', substantially as described and illustrated herein.

* * * * *